US012618778B2

(12) United States Patent
Suzuki

(10) Patent No.: US 12,618,778 B2
(45) Date of Patent: May 5, 2026

(54) GAS CHROMATOGRAPHY COMBUSTION FURNACE/TUBE STRUCTURE FOR A SULFUR CHEMILUMINESCENCE DETECTOR

(71) Applicant: SHIMADZU CORPORATION, Kyoto (JP)

(72) Inventor: Takamasa Suzuki, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 862 days.

(21) Appl. No.: 17/311,721

(22) PCT Filed: Dec. 20, 2018

(86) PCT No.: PCT/JP2018/047046
§ 371 (c)(1),
(2) Date: Jun. 8, 2021

(87) PCT Pub. No.: WO2020/129216
PCT Pub. Date: Jun. 25, 2020

(65) Prior Publication Data
US 2022/0026370 A1     Jan. 27, 2022

(51) Int. Cl.
*G01N 21/76*      (2006.01)
*G01N 33/00*      (2006.01)

(52) U.S. Cl.
CPC ....... *G01N 21/766* (2013.01); *G01N 33/0036* (2013.01); *G01N 33/0073* (2013.01)

(58) Field of Classification Search
CPC ............. G01N 33/0073; G01N 21/766; G01N 33/0036; G01N 30/74; G01N 1/24;
(Continued)

(56) References Cited

U.S. PATENT DOCUMENTS 4,070,155 A  *  1/1978  Fraim ................... G01N 31/005
                                                           436/114
4,090,976 A  *  5/1978  DeHollander ......... C01G 43/01
                                                           423/261
(Continued)

FOREIGN PATENT DOCUMENTS

| CN | 201173899 Y | * | 12/2008 |
|----|-------------|---|---------|
| JP | 57110961 A  | * | 7/1982  |
| JP | 2015-059876 A |  | 3/2015  |

OTHER PUBLICATIONS

Shi, H. et al, Journal of Chromatography A 1997, 779, 307-313 (Year: 1997).*
(Continued)

*Primary Examiner* — Arlen Soderquist
(74) *Attorney, Agent, or Firm* — Sughrue Mion, PLLC

(57)                ABSTRACT
In a sulfur chemiluminescence detector (SCD) including a heating furnace 210 including a combustion tube 211 and a heating means 215 for heating the combustion tube 211, an inert-gas introduction tube 214 that has the front end inserted into an end portion on an inlet side of the combustion tube 211 and has the rear end into which an end portion on the outlet side of a column 140 of a gas chromatograph is inserted, and inert-gas supplying means 264, 221, and 251 for supplying inert gas into the inert-gas introduction tube 214 in a manner that the inert gas flows from the rear end to the front end are provided. The inert gas (for example, nitrogen) flowing through the inert-gas introduction tube 214 can prevent the end portion on the outlet side of the column 140 from being exposed to oxygen. In this manner, generation of column bleeding caused by a decomposition product of the liquid phase can be suppressed, so that a decrease in the sensitivity of the SCD can be suppressed.

2 Claims, 4 Drawing Sheets

(58) Field of Classification Search

CPC .... G01N 1/38; G01N 21/274; G01N 21/6402; G01N 21/643; G01N 21/72; G01N 21/76; G01N 21/77; G01N 30/68; G01N 30/78; G01N 30/84; G01N 31/00; G01N 31/005; G01N 31/12; G01N 33/0013; G01N 33/22; G01N 33/2835; G01N 33/287; G01N 2001/247; G01N 2021/7786; G01N 2030/685; G01N 2030/8405; G01N 2030/8435; G01N 2201/06; Y10T 436/176152; Y10T 436/18; Y10T 436/188; Y10T 436/25125

USPC ........ 436/119–121, 119–122, 153–155, 157, 436/159–161, 171–172, 181; 422/52, 54, 422/89, 91

See application file for complete search history.

(56) References Cited

U.S. PATENT DOCUMENTS

| | | | | |
|---|---|---|---|---|
| 4,193,963 A | * | 3/1980 | Bruening | G01N 21/766 422/89 |
| 4,227,887 A | * | 10/1980 | Takahashi | G01N 33/1826 436/154 |
| 4,244,917 A | * | 1/1981 | Woods | G01N 31/12 432/198 |
| 4,409,336 A | * | 10/1983 | Oita | G01N 31/12 205/785.5 |
| 4,778,764 A | * | 10/1988 | Fine | G01N 31/12 422/89 |
| 4,814,089 A | * | 3/1989 | Kumar | G01N 30/28 95/82 |
| 4,916,077 A | * | 4/1990 | Forster | G01N 31/12 261/78.2 |
| 4,950,456 A | * | 8/1990 | Forster | G01N 31/12 261/78.2 |
| 5,073,753 A | * | 12/1991 | Collings | G01N 27/626 436/154 |
| 5,501,981 A | * | 3/1996 | Ray | G01N 30/68 436/119 |
| 5,614,417 A | * | 3/1997 | Kubala | G01N 33/287 436/119 |
| 5,916,523 A | * | 6/1999 | Yan | G01N 21/766 422/52 |
| 6,458,328 B1 | * | 10/2002 | Wreyford | G01N 31/12 422/89 |
| 2003/0049855 A1 | * | 3/2003 | Rhodes | G01N 33/0014 436/117 |
| 2004/0126729 A1 | * | 7/2004 | Hayashi | G01N 31/12 432/66 |
| 2005/0074365 A1 | * | 4/2005 | Olstowski | G01N 33/287 436/119 |
| 2005/0129578 A1 | * | 6/2005 | Olstowski | G01N 33/2835 436/160 |
| 2005/0153253 A1 | * | 7/2005 | Olstowski | F23M 9/06 431/76 |
| 2010/0047917 A1 | * | 2/2010 | Akasaka | G01N 21/75 422/94 |
| 2014/0017129 A1 | * | 1/2014 | Miki | G01N 33/0013 423/242.1 |
| 2019/0383748 A1 | * | 12/2019 | Barendregt | G01N 21/766 |
| 2020/0003695 A1 | * | 1/2020 | Horiike | B01L 3/508 |
| 2020/0249170 A1 | * | 8/2020 | Yamane | G01N 21/76 |
| 2021/0285886 A1 | * | 9/2021 | Barendregt | G01N 21/766 |
| 2021/0404999 A1 | * | 12/2021 | Kozakura | G01N 21/76 |
| 2022/0026370 A1 | * | 1/2022 | Suzuki | G01N 33/0073 |
| 2022/0026406 A1 | * | 1/2022 | Li | B01D 53/025 |

OTHER PUBLICATIONS

Agilent 355 Sulfur and 255 Nitrogen Chemiluminescence Detectors Operation and Mantainance Manual 2012, 120 pages. (Year: 2012).*

Agilent 8355 S Sulfur and 8255 S Nitrogen Chemiluminescence Detectors User Manual 2017, 110 pages. (Year: 2017).*

Meier-Augenstein, W., Rapid Communications in Mass Spectrometry 1997, 11, 1775-1780. (Year: 1997).*

Written Opinion of PCT/JP2018/047046 dated Mar. 19, 2019 [PCT/ISA/237].

International Search Report of PCT/JP2018/047046 dated Mar. 19, 2019 [PCT/ISA/210].

* cited by examiner 271 241 121 110
131
240 120 130
200 100

263 262 261
H₂ O₂ N₂

O₂ FLOW CONTROLLER 237

266 265 H₂ O₂ N₂ 264
210
267 250 140
← SAMPLE GAS
212 252
211 213 215 214

234 233 238
OZONE O₃ REACTION LIGHT-EMISSION CONTROLLER/
GENERATOR CELL DETECTOR PROCESSOR
231 232

OZONE VACUUM → EXHAUST
SCRUBBER PUMP
235 236

GAS CHROMATOGRAPHY COMBUSTION FURNACE/TUBE STRUCTURE FOR A SULFUR CHEMILUMINESCENCE DETECTOR

TECHNICAL FIELD

The present invention relates to a sulfur chemiluminescence detector.

BACKGROUND ART

The sulfur chemiluminescence detector (SCD) is capable of detecting a sulfur compound in a sample at high sensitivity by using chemiluminescence, and is usually used in combination with a gas chromatograph (GC) (see Patent Literature 1, for example).

Gas containing sample components (sample gas) separated in a column of the GC is introduced into a heating furnace provided in the SCD. The heating furnace includes a combustion tube and a heater for heating the combustion tube. The sample gas is oxidized while passing through the combustion tube, and sulfur dioxide ($SO_2$) is generated from a sulfur compound in the sample gas. Furthermore, the $SO_2$ is reduced while passing through the combustion tube, and sulfur monoxide (SO) is generated from the $SO_2$. The SO is introduced into a reaction cell provided in the subsequent stage of the heating furnace and mixed with ozone ($O_3$) in the reaction cell. The reaction of SO and $O_3$ produces an excited species ($SO_2^*$) of sulfur dioxide. When the $SO_2^*$ turns back to the ground state through chemiluminescence, the emission intensity of the $SO_2^*$ is detected by a photodetector, and thus the quantity of the sulfur compound contained in the sample gas is detected from the emission intensity.

CITATION LIST

Patent Literature

Patent Literature 1: JP 2015-59876 A

SUMMARY OF INVENTION

Technical Problem

When the SCD is used in combination with the GC as described above, gas chromatography is performed in a state where an outlet end of the column of the GC is inserted into an inlet of the combustion tube in the heating furnace of the SCD. At this time, the temperature near the inlet of the combustion tube is about 450 to 500° C.

However, the heat-resistant temperature of a general GC column is about 400° C.; and it is known that, when the GC column is used over the heat-resistant temperature, a part of the stationary phase (usually liquid phase) of the column is decomposed and a decomposition product (cyclic siloxane, and the like) elutes from the column to generate a background signal called column bleeding. Since this column bleeding deteriorates the SN ratio and causes a decrease in the sensitivity of the SCD, an effective measures for reducing the column bleeding is required.

The present invention has been developed in view of the above points, and an object of the present invention is to provide an SCD capable of reducing column bleeding and minimizing a decrease in the sensitivity due to the column bleeding.

Solution to Problem

A sulfur chemiluminescence detector (SCD) according to the present invention developed to solve the above problem includes:

a heating furnace including a combustion tube and a heating means for heating the combustion tube:

an inert-gas introduction tube having a front end configured to be inserted into an end portion on an inlet side of the combustion tube and having a rear end configured so that an end portion on an outlet side of a column of a gas chromatograph is inserted; and an inert-gas supplying means configured to supply inert gas into the inert-gas introduction tube in a manner that the inert gas flows from the rear end to the front end.

Cyclic siloxane, which causes column bleeding, is produced in a case where a liquid phase of the column is exposed to oxygen at high temperatures. Oxygen (or air) is introduced into the combustion tube of the heating furnace as an oxidizing agent to oxidize sample gas eluted from the column. In a conventional SCD, an end portion on the outlet side of a column (GC column) of a gas chromatograph is directly inserted into an end portion on the inlet side of a combustion tube. For this reason, a liquid phase of the GC column is exposed to oxygen inside the combustion tube, resulting in column bleeding. In contrast, in the SCD according to the present invention, the front end of the inert-gas introduction tube is inserted into the end portion on the inlet side of the combustion tube, and the end portion on the outlet side of the GC column is inserted into the rear end of the inert-gas introduction tube. Since the inert gas flows through the inert-gas introduction tube from the rear end to the front end, with the tip of the end portion on the outlet side of the GC column being located inside the inert-gas introduction tube, the liquid phase of the GC column is not exposed to oxygen present in the combustion tube. As a result, the occurrence of column bleeding can be suppressed in the SCD according to the present invention.

It is desirable to use nitrogen as the inert gas in the present invention. Other inert gas (for example, helium) can also be used.

In the sulfur chemiluminescence detector according to the present invention, the tip of the end portion on the outlet side of the column is preferably located at a position retracted from the front end of the inert-gas introduction tube inside the inert-gas introduction tube.

Advantageous Effects of Invention

As described above, according to the sulfur chemiluminescence detector according to the present invention having the above configuration, the occurrence of column bleeding can be suppressed, and, in this manner, a decrease in the sensitivity caused by the column bleeding can be minimized.

DESCRIPTION OF EMBODIMENTS

Figures 1, 2:
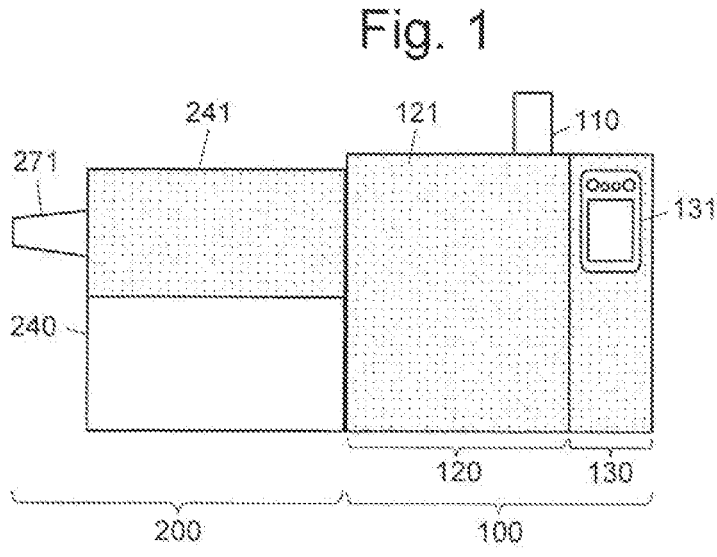
FIG. 1 is a front view showing the appearance of a GC system including an SCD according to an embodiment of the present invention.
FIG. 2 is a diagram showing a configuration of a main part of the SCD.
Figures 3, 4:
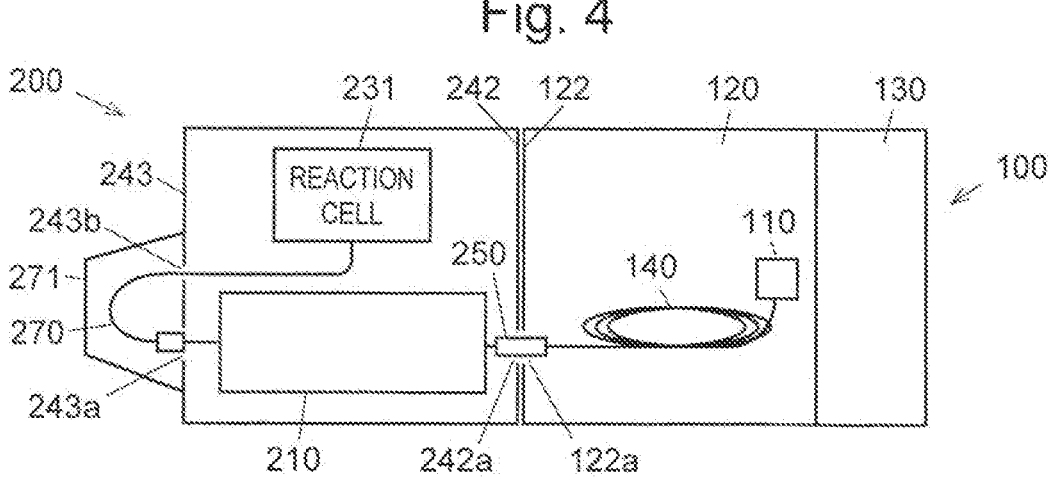
FIG. 3 is a front view schematically showing an inner configuration of the GC system.
FIG. 4 is a top view schematically showing the inner configuration of the GC system.
Figure 5:
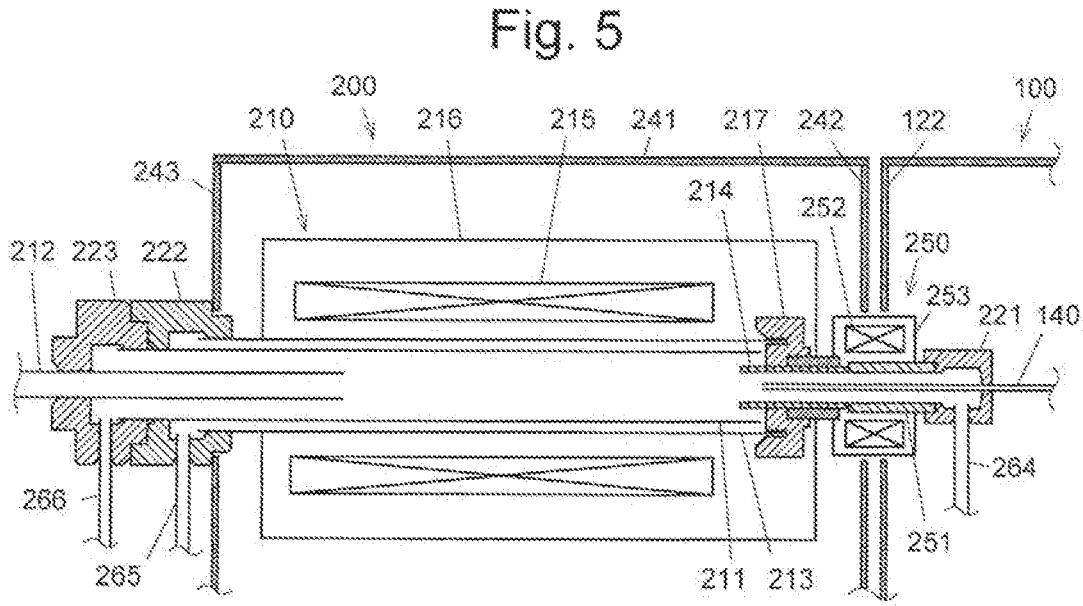
FIG. 5 is a cross sectional view showing a configuration around a heating furnace of the SCD.

A configuration for performing the present invention is described hereinafter, with reference to the drawings. FIG. 1 is a front view showing the appearance of a gas chromatograph system (GC system) including a sulfur chemiluminescence detector (SCD) according to the present embodiment. FIG. 2 is a diagram showing a configuration of a main part of the SCD according to the present embodiment. FIG. 3 and FIG. 4 are schematic view showing an inner configuration of the GC system, and FIG. 3 is a front view and FIG. 4 is a top view. FIG. 5 is a cross sectional view showing a configuration around a heating furnace of the SCD.

A GC 100 includes a sample introduction unit 110, a column oven 120 that contains and heats a column 140, and a control-board container 130 in which a control board (not shown) and the like are contained. A front face of the column oven 120 is an openable and closable door 121, and a front face of the control-board container 130 is provided with an operation panel 131.

In the GC 100, a sample is introduced into the flow of carrier gas at the sample introduction unit 110, and the carrier gas containing the sample is introduced into an inlet end of the column 140 contained in the column oven 120. The sample is separated into components in the process of passing through the column 140. Gas (hereinafter, referred to as the "sample gas") containing each of the separated sample components is sequentially eluted from an outlet end of the column 140.

As shown in FIG. 2, an SCD 200 includes a heating furnace 210, a reaction cell 231, an optical filter 232, a light-emission detector 233, an ozone generator 234, an ozone scrubber 235, a vacuum pump 236, a flow controller 237, a controller/processor 238, and an enclosure 240 (see FIG. 1) that contains these. Furthermore, the SCD 200 includes an interface 250 that is located at the boundary with the GC 100 and is for connecting the SCD 200 and the GC 100.

As shown in FIGS. 3 and 4, the heating furnace 210 is contained in the SCD 200, at the upper front side of the enclosure 240 of the SCD 200, and the reaction cell 231 and other constituents (omitted in FIGS. 3 and 4) are contained in the remaining area inside the enclosure 240 (for example, below or behind the heating furnace 210). Note that the top face of the space where the heating furnace 210 is contained is a door 241 (see FIG. 1) that is openable and closable, in the enclosure 240 of the SCD 200.

As shown in FIG. 5, the heating furnace 210 includes an exterior combustion tube 211 (corresponding to the "combustion tube" of the present invention), an interior combustion tube 212, an oxidizing-agent supply tube 213, an inert-gas introduction tube 214, a heater 215 (corresponding to the "heating means" of the present invention), and a housing 216 containing these. Hereinafter, of each of the pipelines shown in FIG. 5, that is, the exterior combustion tube 211, the interior combustion tube 212, the oxidizing-agent supply tube 213, the inert-gas introduction tube 214, and a tube 251 (described later), an end portion located on the left side in the diagram will be referred to as the "left end" of each pipeline, and an end portion located on the right side in the diagram will be referred to as the "right end" of each pipeline.

The exterior combustion tube 211 is located inside the oxidizing-agent supply tube 213 coaxially with the oxidizing-agent supply tube 213, and the inert-gas introduction tube 214 has the left end ("front end" in the present invention) inserted into the right end ("end portion on the inlet side" in the present invention) of the exterior combustion tube 211. The interior combustion tube 212 has its right end inserted into the left end of the exterior combustion tube 211. The exterior combustion tube 211, the interior combustion tube 212, the oxidizing-agent supply tube 213, and the inert-gas introduction tube 214 are each made from ceramic, such as alumina.

A connector 217 is attached to the right ends of the oxidizing-agent supply tube 213 and the exterior combustion tube 211. The inert-gas introduction tube 214 is inserted through the connector 217. An opening portion at the right end of the oxidizing-agent supply tube 213 and the exterior combustion tube 211 is closed by the connector 217. However, a groove is provided on a left end surface of the connector 217, and gas can flow between the oxidizing-agent supply tube 213 and the exterior combustion tube 211 through the groove. The inert-gas introduction tube 214 has the right end ("rear end" in the present invention) that protrudes from the housing 216 of the heating furnace 210, and is connected to the left end of the tube 251 provided inside the interface 250 located at the boundary between the GC 100 and the SCD 200. The interface 250 includes, in addition to the tube 251, a heater 252 configured to heat the tube 251, and a housing 253 containing the tube 251 and the heater 252. The interface 250 is inserted through an opening 242*a* provided in a right wall 242 of the enclosure 240 of the SCD 200 as well as through an opening 122*a* provided in a left wall 122 of the enclosure of the GC 100. The right end of the tube 251 protrudes from the housing 253 of the interface 250, and a first joint 221 is attached to the right end. To the first joint 221, an inert-gas passage 264 used for supplying inert gas (in this case, nitrogen) to the inert-gas introduction tube 214 is connected. The first joint 221 is provided with an aperture (not shown) through which the column 140 of the GC 100 is inserted. An end portion on the outlet side of the column 140 is inserted through the aperture into the first joint 221, passes through the tube 251 in the interface 250, and is finally inserted in the interior of the heating furnace 210, specifically, the interior of the inert-gas introduction tube 214. At this time, the outlet end ("tip of an end portion on the outlet side" in the present invention) of the column 140 is located at a position slightly retracted from the front end of the inert-gas introduction tube 214.

In contrast, the left ends of the oxidizing-agent supply tube 213, the exterior combustion tube 211, and the interior combustion tube 212 protrude from the housing 216 of the heating furnace 210, and further protrude to the outside from an opening 243*a* provided in a left wall 243 of the enclosure 240 of the SCD 200. In the exterior of the enclosure 240, a second joint 222 is attached to the left end of the oxidizing-agent supply tube 213. To the second joint 222, an oxidizing-agent passage 265 used for supplying an oxidizing agent (in this case, oxygen) to the oxidizing-agent supply tube 213 is connected. The exterior combustion tube 211 is inserted through the second joint 222, and a third joint 223 is attached to the left end of the exterior combustion tube 211. A reducing-agent passage 266 for supplying a reducing agent (hydrogen in this case) to the exterior combustion tube 211 is connected to the third joint 223. The interior combustion tube 212 is inserted through the third joint 223 and has its left end connected to a transportation tube 270 that extends to the reaction cell 231.

The transportation tube 270 is formed of a flexible tube, which turns back in the exterior of the enclosure 240 of the SCD 200 to again enter the interior of the enclosure 240 through another opening 243*b* (see FIG. 4) provided in the left wall 243 of the enclosure 240, and is connected to the reaction cell 231 in the enclosure 240. The outer face of the left wall 243 of the SCD 200 is provided with an openable cover 271 at a position where the cover 271 is capable of covering the openings 243*a* and 243*b*, though the cover 271 is not shown in FIG. 5.

The inert-gas passage 264, the oxidizing-agent passage 265, and the reducing-agent passage 266 are all connected to the flow controller 237, and the flow controller 237 controls a flow rate of gas supplied from an inert-gas supply source 261, an oxidizing-agent supply source 262, and a reducing-agent supply source 263 to the inert-gas passage 264, the oxidizing-agent passage 265, and the reducing-agent passage 266, respectively. The inert-gas supply source 261, the oxidizing-agent supply source 262, and the reducing-agent supply source 263 can be composed of, for example, a gas cylinder or the like filled with nitrogen, oxygen, and hydrogen, respectively.

Nitrogen supplied from the inert-gas supply source 261 to the inert-gas passage 264 through the flow controller 237 flows in the right end (rear end) of the inert-gas introduction tube 214 through the first joint 221 and the tube 251, and flows from the right end (rear end) toward the left end (front end) in the inert-gas introduction tube 214. That is, the inert-gas passage 264, the first joint 221 and the tube 251 in the present embodiment correspond to the "inert-gas supplying means" in the present invention. In the present embodiment, nitrogen is used as the inert gas. However, other inert gas (for example, helium) can also be used.

Oxygen supplied from the oxidizing-agent supply source 262 to the oxidizing-agent passage 265 through the flow controller 237 flows in the left end of the oxidizing-agent supply tube 213 through the second joint 222, and flows toward the right side in a space between the inner wall of the oxidizing-agent supply tube 213 and the outer wall of the exterior combustion tube 211. The oxygen that reaches the right end of the oxidizing-agent supply tube 213 flows into the exterior combustion tube 211 through the groove (described above) formed in the left end face of the connector 217, and then flows toward the left side in the exterior combustion tube 211. In the present embodiment, oxygen is used as the oxidizing agent. However, air can also be used as the oxidizing agent.

Hydrogen supplied from the reducing-agent supply source 263 to the reducing-agent passage 266 through the flow controller 237 flows in the left end of the exterior combustion tube 211 through the third joint 223, and flows toward the right side in a space between the inner wall of the exterior combustion tube 211 and the outer wall of the interior combustion tube 212. The hydrogen that reaches the right end of the interior combustion tube 212 is drawn into the interior combustion tube 212 at this right end of the interior combustion tube, and flows toward the left side in the interior combustion tube 212.

A sample gas introduced from the outlet end of the column 140 of the GC 100 into the interior of the heating furnace 210 is mixed with the oxygen at the right end of the exterior combustion tube 211, and is oxidatively decomposed at high temperature while the mixed gas is flowing in the exterior combustion tube 211 toward the left. At this time, if the sample component is a sulfur compound, sulfur dioxide is generated. The gas containing the sample component that has undergone the oxidative decomposition is drawn into the interior combustion tube 212 with the hydrogen introduced from the vicinity of the left end of the exterior combustion tube 211. In the case where sulfur dioxide is contained in the sample component that has undergone the oxidative decomposition, the sulfur dioxide reacts with the hydrogen at this stage, so as to be reduced to sulfur monoxide. The gas that has passed through the interior combustion tube 212 is introduced in the reaction cell 231 through the transportation tube 270.

The gas sent from the transportation tube 270 to the reaction cell 231 is mixed with ozone inside the reaction cell 231. At this time, chemiluminescence generated by the reaction between the sulfur monoxide and ozone is detected by the light-emission detector 233 including a photomultiplier tube and other components, through the optical filter 232. The ozone is generated in the ozone generator 234 using oxygen supplied from the oxidizing-agent supply source 262 through an oxygen passage 267, and is supplied to the reaction cell 231. At this time, the flow rate of the oxygen to be supplied to the ozone generator 234 through the oxygen passage 267 is also controlled by the flow controller 237. The ozone scrubber 235 and the vacuum pump 236 are provided downstream of the reaction cell 231. The gas inside the reaction cell 231, which is sucked by the vacuum pump 236, is discharged to the outside, after ozone in the gas is removed by the ozone scrubber 235.

Detection signals from the light-emission detector 233 are sent to the controller/processor 238, and the concentration of the sulfur compound in the sample gas is calculated based on the detection signals in the controller/processor 238. The controller/processor 238 is embodied by a microcomputer including CPU, ROM, RAM and an input-output circuit for performing communication with external peripheral devices, for example. Calculation processing in accordance with a control program and a control parameter which are stored in the ROM, for example, is executed mainly by the CPU, so that processing of the detection signals is performed and the operation of each unit is controlled. Specifically, the heater 215 of the heating furnace 210, the heater 252 of the interface 250, the light-emission detector 233, the ozone generator 234, the vacuum pump 236, the flow controller 237, and other devices are controlled.

In order to promote the oxidation-reduction reaction in each of the exterior combustion tube 211 and the interior combustion tube 212, the interior of the heating furnace 210 is heated by the heater 215 to 500° C. or more (preferably 700° C. to 1200° C.) in an area where the temperature is the highest. Further, at this time, the temperature near the inlet of the heating furnace 210 is about 450° C. to 500° C.

The temperature near the inlet exceeds the heat-resistant temperature (about 400° C.) of a capillary column generally used as the column 140 of a GC, that is, a column formed by applying a stationary phase (liquid phase) to an inner wall of a fused quartz tube. In a case where the liquid phase of the column 140 is exposed to oxygen at such a temperature, a part of the liquid phase is decomposed, and a decomposition product of the decomposition causes column bleeding.

Figure 6:
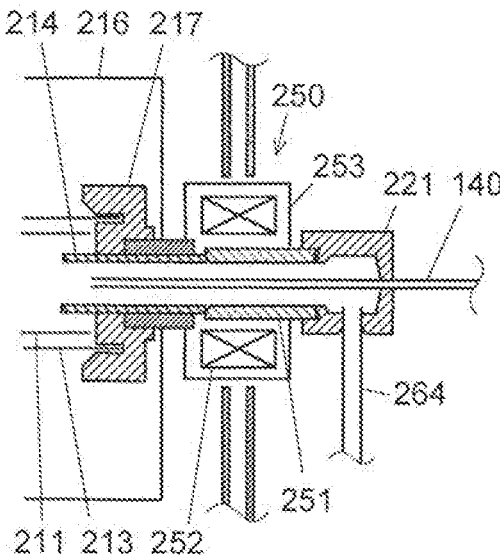
FIG. 6 is an enlarged cross-sectional view showing a configuration near an inlet of the heating furnace.
Figure 7:
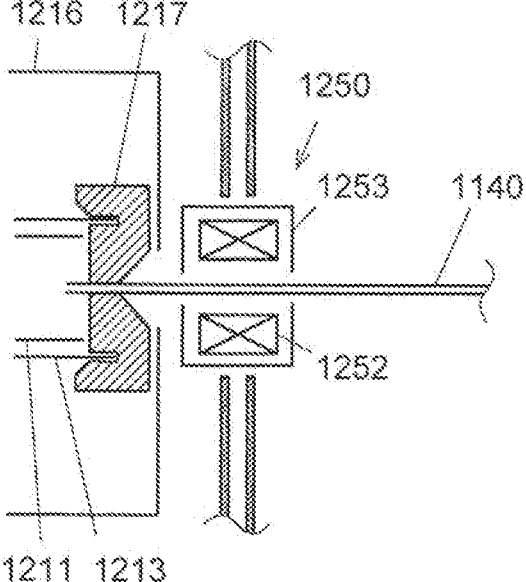
FIG. 7 is a cross-sectional view showing a configuration near an inlet of a heating furnace in a conventional SCD.

The inert-gas introduction tube 214 in the SCD of the present embodiment is provided to suppress this column bleeding. FIG. 6 shows an enlarged view of the vicinity of the inlet of the heating furnace in the SCD of the present embodiment, and FIG. 7 shows an enlarged view of the vicinity of an inlet of a heating furnace in a conventional SCD. In FIG. 7, the same or corresponding constituents to those in FIG. 6 are designated by a reference numeral having the last three digits that are common.

In the conventional SCD, as shown in FIG. 7, since an end portion on the outlet side of a column 1140 is directly inserted into the right end (end portion on the inlet side) of an exterior combustion tube 1211, the liquid phase of the column 1140 is exposed to an oxidizing agent (oxygen or air) introduced, through an oxidizing-agent supply channel 1213, to the vicinity of the right end of the exterior combustion tube 1211, which has caused column bleeding. In contrast, in the SCD according to the present embodiment, as shown in FIG. 6, the front end of the inert-gas introduction tube 214 is inserted into the end portion on the inlet side of the exterior combustion tube 211, the outlet end of the column 140 is inserted into the inert-gas introduction tube 214 through the rear end of the inert-gas introduction tube 214, and the tip of the column 140 is located at a position slightly retracted from the front end of the inert-gas introduction tube 214. Since the inert gas (nitrogen) flows through the inert-gas introduction tube 214 from the rear end to the front end as described above, the outlet end of the column 140 is located in the flow of the inert gas and is not exposed to oxygen or air existing in the exterior combustion tube 211. For this reason, even if the column 140 is placed under high temperature, the occurrence of column bleeding can be suppressed and a decrease in the sensitivity of the SCD can be minimized.

Furthermore, since the residence time of the sample gas in the exterior combustion tube 211 can be shortened by the flow of the inert gas, the effect of preventing the exterior combustion tube 211 from being contaminated by a metal component or the like contained in the sample gas is also obtained.

Further, in a case where nitrogen is used as the inert gas, nitrogen supplied from the front end of the inert-gas introduction tube 214 into the exterior combustion tube 211 promotes a redox reaction inside the exterior combustion tube 211 and the interior combustion tube 212, and as a result, the effect of stabilizing the sensitivity of the SCD is also obtained.

Although the embodiment of the present invention is described with specific examples, the present invention is not limited to such an embodiment, and an appropriate change in the scope of the present invention is acceptable. For example, although the present invention is applied to the SCD including a horizontal-type heating furnace (i.e., a heating furnace containing in its interior a combustion tube extending in the horizontal direction) in the aforementioned embodiment, the present invention is not limited to be applied to such a horizontal-type heating furnace. The present invention can also be applied to an SCD provided with a vertical-type heating furnace (i.e., a heating furnace containing in its interior a combustion tube extending in the vertical direction) as disclosed in Patent Literature 1.

REFERENCE SIGNS LIST

100 . . . GC
110 . . . Sample Introduction Unit
120 . . . Column Oven
130 . . . Control-Board Container
140 . . . Column
200 . . . SCD
210 . . . Heating Furnace
211 . . . Exterior Combustion Tube
212 . . . Interior Combustion Tube
213 . . . Oxidizing-Agent Supply Tube
214 . . . Inert-Gas Introduction Tube
215 . . . Heater
216 . . . Housing
231 . . . Reaction Cell
232 . . . Optical Filter
233 . . . Light-Emission Detector
234 . . . Ozone Generator
235 . . . Ozone Scrubber
236 . . . Vacuum Pump
237 . . . Flow Controller
238 . . . Controller/Processor
240 . . . Enclosure
250 . . . Interface
251 . . . Tube
252 . . . Heater
253 . . . Housing

The invention claimed is:

1. A sulfur chemiluminescence detector comprising:
a heating furnace including a combustion tube and a heating means for heating the combustion tube;
an inert-gas introduction tube having a front end configured to be inserted into an end portion on an inlet side of the combustion tube and having a rear end configured so that an end portion on an outlet side of a column of a gas chromatograph is inserted;
an oxidizing-agent supply configured to supply an oxidizing-agent into the combustion tube; and
an inert-gas supply configured to supply inert gas into the inert-gas introduction tube in a manner that the inert gas flows from the rear end to the front end,
wherein a tip of an end portion on the outlet side of the column is located at a position retracted from the front end of the inert-gas introduction tube inside the inert-gas introduction tube.

2. The sulfur chemiluminescence detector according to claim 1, wherein the inert gas is nitrogen.

* * * * *